US009025154B2

(12) United States Patent  
Alameh et al.

(10) Patent No.: US 9,025,154 B2  
(45) Date of Patent: May 5, 2015

(54) DEVICE FOR SELECTING A SPECIFIC MATTER

(75) Inventors: Kamal Alameh, Rivervale (AU); Sreten Askraba, Quinns Rocks (AU)

(73) Assignee: Photonic Detection Systems PTY Ltd., Subiaco (AU)

( * ) Notice: Subject to any disclaimer, the term of this patent is extended or adjusted under 35 U.S.C. 154(b) by 140 days.

(21) Appl. No.: 13/698,964

(22) PCT Filed: Apr. 20, 2011

(86) PCT No.: PCT/AU2011/000448  
§ 371 (c)(1),  
(2), (4) Date: Feb. 18, 2013

(87) PCT Pub. No.: WO2011/143686  
PCT Pub. Date: Nov. 24, 2011

(65) Prior Publication Data  
US 2013/0141728 A1 Jun. 6, 2013

(30) Foreign Application Priority Data  
May 18, 2010 (AU) ................................ 2010902165

(51) Int. Cl.  
*G01N 21/55* (2014.01)  
*G01N 21/31* (2006.01)

(52) U.S. Cl.  
CPC ............ *G01N 21/55* (2013.01); *G01N 21/3151* (2013.01); *G01N 2021/3148* (2013.01)

(58) Field of Classification Search  
CPC .............. G01N 21/55; G01N 21/3151; G01N 2021/3148; G01J 3/50  
USPC ................... 356/445, 446, 420; 250/221, 226  
See application file for complete search history.

(56) References Cited

U.S. PATENT DOCUMENTS 5,389,781 A * 2/1995 Beck et al. ................... 250/226  
6,009,186 A 12/1999 Gorretta et al.  
(Continued)

FOREIGN PATENT DOCUMENTS

WO 2008014553 A1 2/2008

OTHER PUBLICATIONS

Supplementary European Search Report for EP Appln. No. 11782752.7, dated Oct. 1, 2013.  
(Continued)

*Primary Examiner* — Hoa Pham  
*Assistant Examiner* — Isiaka Akanbi  
(74) *Attorney, Agent, or Firm* — Locke Lord LLP; Jeffrey D. Hsi

(57) ABSTRACT

The present disclosure provides an optical device for selecting specific matter, such as plant matter. The device comprises a light source for emitting light having at least (3) wavelengths and for generating a combined beam of light having the at least 3 wavelengths. The device further comprises an optical element for directing a plurality of light beams towards matter including the specific matter. The optical element has first surface portions through which in use the plurality of component light beams are directed to the matter including the specific matter. Each component light beam is directed through a respective first surface portion that has an optical property that is selected so that light intensity differences between the component light beams are reduced. The optical device also comprises an optical filter for filtering reflected component light beams such that an intensity of light is reduced in a wavelengths range outside one or more wavelengths ranges that include the at least three wavelengths. Further, the optical device comprises a detector for detecting the reflected component light beams.

16 Claims, 4 Drawing Sheets

(56) References Cited

U.S. PATENT DOCUMENTS

| | | | |
|---|---|---|---|
| 7,081,611 B2* | 7/2006 | Scott | 250/221 |
| 2008/0170385 A1* | 7/2008 | Bock et al. | 362/125 |
| 2012/0105852 A1* | 5/2012 | Patil et al. | 356/445 |

OTHER PUBLICATIONS

Sahba, Kaveh et al.; "Photonics-Based Spectral Reflectance Sensor for Plant Discrimination"; Optical Internet, Jun. 24, 2007, pp. 1-3.

* cited by examiner

DEVICE FOR SELECTING A SPECIFIC MATTER

CROSS-REFERENCES TO RELATED APPLICATIONS

This application is a 35 U.S.C. §371 U.S. national entry of International Application PCT/AU2011/000448 (WO2011/143686 A1) having an International filing date of Apr. 20, 20115, 2011, which claims under 35 U.S.C. §119(a) the benefit of Australian Application No. 2010-902165, filed May 18, 2010, the entire contents of which are incorporated herein by reference.

FIELD OF THE INVENTION

The present invention broadly relates to a device for selecting specific matter, such as plant matter.

BACKGROUND

The control of weed growth is an important factor in agriculture. Large areas of plant matter including valuable plants, such as crops, and weeds are usually sprayed with expensive and toxic chemicals in order to control the weed growth. However, ideally only the weeds should be sprayed, but this is difficult if the weeds grow amongst the valuable plant matter. An automated device that is able to distinguish weeds from the valuable plant matter in a quick manner could be used to restrict the spraying of the chemicals to the weeds only and consequently would offer a significant commercial advantage.

Further, it is also of general advantage to be able to distinguish in an automated manner particular plant matter from other matter so that the particular plant matter can be treated differently to the other matter.

PCT International Application Number PCT/AU2007/001075, also owned by the present applicant, discloses an optical device for discriminating specific plant matter from other matter. The optical device comprises laser diodes that emit light having three wavelengths and a plurality of light beams. Each light beam has the three wavelengths directed to the plant matter. A detector detects light beams that are reflected back from the plant matter. A processor then processes the reflected intensities and compares the detected intensity ratios at the three wavelengths with a library of such intensity ratios of known plant matter whereby the device is enabled to discriminate a particular type of plant matter from other matter.

The present disclosure provides a further technological improvement.

SUMMARY OF THE INVENTION

The present invention provides in a first aspect an optical device for selecting specific matter, the device comprising:
 a light source for emitting light having at least 3 wavelengths and for generating a combined beam of light having the at least 3 wavelengths;
 an optical element for receiving the combined beam of light and directing a plurality of component light beams towards matter including the specific matter, the optical element having first surface portions through which in use the plurality of component light beams are directed to the matter including the specific matter, the first surface portions having optical properties that are selected so that light intensity differences between the component light beams are reduced;
 an optical filter for filtering component light beams that were reflected by the matter including the specific matter, the filter being arranged such that an intensity of the reflected light is reduced in a wavelengths range outside one or more wavelengths ranges that include the at least three wavelengths; and
 a detector for detecting the reflected and filtered component light beams.

The specific matter typically is plant matter, such as plant leaves, fruit or weeds, but may alternatively also be any other type of matter, such as minerals or another type of organic matter. Further, the specific matter may for example be fruit having a specific property, such as ripens, and the optical device may be arranged to select the fruit having that property from other fruit that does not have that property.

The optical device typically is arranged such that each component light beam is directed through a respective first surface portion.

In one specific embodiment the optical element is arranged to distribute light intensity from the light source into the plurality of component light beams so that the component beams of light have substantially same intensity. The component light beams typically are substantially parallel.

Embodiments of the present invention have significant practical advantages that improve both the sensitivity and the range of detection of the device. The optical element is arranged such that intensity differences between the (outgoing) component light beams are reduced. Consequently, the likelihood that light intensity differences of reflected component light beams are a result of influences other than differences in reflectivity between a particular type of specific matter and other matter is reduced.

Further, the optical filter is arranged for filtering a reflected intensity of light such that an intensity of light in a wavelength range outside wavelength ranges that include the at least three wavelengths is reduced. For example, during use of the device, shading may result in differences in daylight intensities to which specific matter and other matter is exposed. This results in fluctuating background intensity for the reflected light during movement of the device over the matter. Consequently, the optical filter and the optical element together typically are arranged so that light intensity differences arising from influences other than the reflectivity of the matter are reduced, which improves the sensitivity and the range of detection of the device.

The optical element typically comprises also second surface portions that are substantially parallel to respective first surface portions. The first and second surface portions typically have reflective coatings. The first and second surface portions typically are arranged such that a combined beam of light having the at least three wavelengths ranges is reflected between the first and second surface portions in a zigzag manner.

The optical properties of the first surface portions typically are transmisivities that are selected such that a portion of the combined beam of light penetrates through the first surface portions thereby forming a series of component beams of light.

The optical device typically comprises adjacent first surface portions that have respective optical properties. The optical properties may be largely uniform within each first surface portion. The first surface portions typically form a sequence of first surface portions each having a respective transmissivity. For example, each first surface portion may have a reflective coating that has a respective transmissivity.

In an alternative embodiment the first surface portions of the optical element may each have a transmissivity that changes along at least a portion of a length of the optical element in a substantially continuous manner.

In one specific embodiment the optical element comprises a prism that is optically transparent, such as a suitable glass prism. The prism typically is a rectangular prism and the first and second surface portions are opposite surface portions of the rectangular prism. The prism typically has two end portions and the device typically is arranged such that the combined laser light is coupled into the prism near one end portion and is then reflected between the first and second surface portions in a zigzag manner.

In one specific embodiment the first surface portions are arranged such that a series of component light beams transmits through the first surface portions and the component light beams have substantially the same intensity. In this embodiment the first surface portions have a transmissivities that typically increases in one direction along a series of the first surface portions. For example, the optical component may be a rectangular prism and the combined light is coupled into the prism at one end portion of the prism. The first surface portions may have respective average transmissivities that increase along a length of the prism and in a direction away from the end portion at which the light is coupled into the prism.

The optical element typically comprises a layered structures of a dielectric material having properties selected so that desired transmissivity properties are achieved at a wavelengths range that includes the at least three wavelengths of light emitted by the light source.

The optical filter typically is a band pass filter that is arranged to allow transmission of light having a predetermined wavelength range. In this embodiment the optical filter is arranged so that the predetermined wavelength range includes the at least three wavelengths of light emitted by the light source. For example, the optical filter may be arranged to have one, two or more windows through which in use light passes through to the detector.

The optical light source typically comprises lasers, such as three lasers which provide light having respective wavelengths or wavelength ranges. A first wavelength may be in the range of 600-650 nm, such as 635 nm, a second wavelength may be in the range of 650-700 nm, such as 670 nm and a third wavelength may be in the range of 700-850 nm, such as 785 nm. Further, the optical light source typically comprises a combiner that is arranged to combine emitted light into the combined beam of light having the at least three wavelengths.

The optical device typically comprises a processor for processing signals from the detector and selecting the specific matter. The device typically is arranged for movement over the matter including the specific matter and may also comprise components for selectively treating selected specific matter.

The present invention provides in a second aspect an optical device for selecting specific matter, the device comprising:
 a light source for emitting light having at least 3 wavelengths and for generating a combined beam of light having the at least 3 wavelengths;
 an optical element for receiving the combined beam of light and directing a plurality of component light beams towards matter including the specific matter, the optical element having first surface portions through which the component light beams are directed to matter including the specific matter, each first surface portion having an optical property that is selected so that light intensity differences between the component light beams are reduced; and
 a detector for detecting reflected component light beams.

The specific matter typically is plant matter, such as plant leaves, fruit or weeds, but may alternatively also be any other type of matter, such as minerals or another type of organic matter. Further, the specific matter may for example be fruit having a specific property, such as ripens, and the optical device may be arranged to select the fruit having that property from other fruit that does not have that property.

The invention will be more fully understood from the following description of specific embodiments of the invention. The description is provided with reference to the accompanying drawings.

DETAILED DESCRIPTION OF SPECIFIC EMBODIMENTS

PCT International Application Number PCT/AU2007/001075, owned by the present applicant, discloses an optical device for discriminating plant matter and is hereby incorporated by cross-reference.

Figure 1:
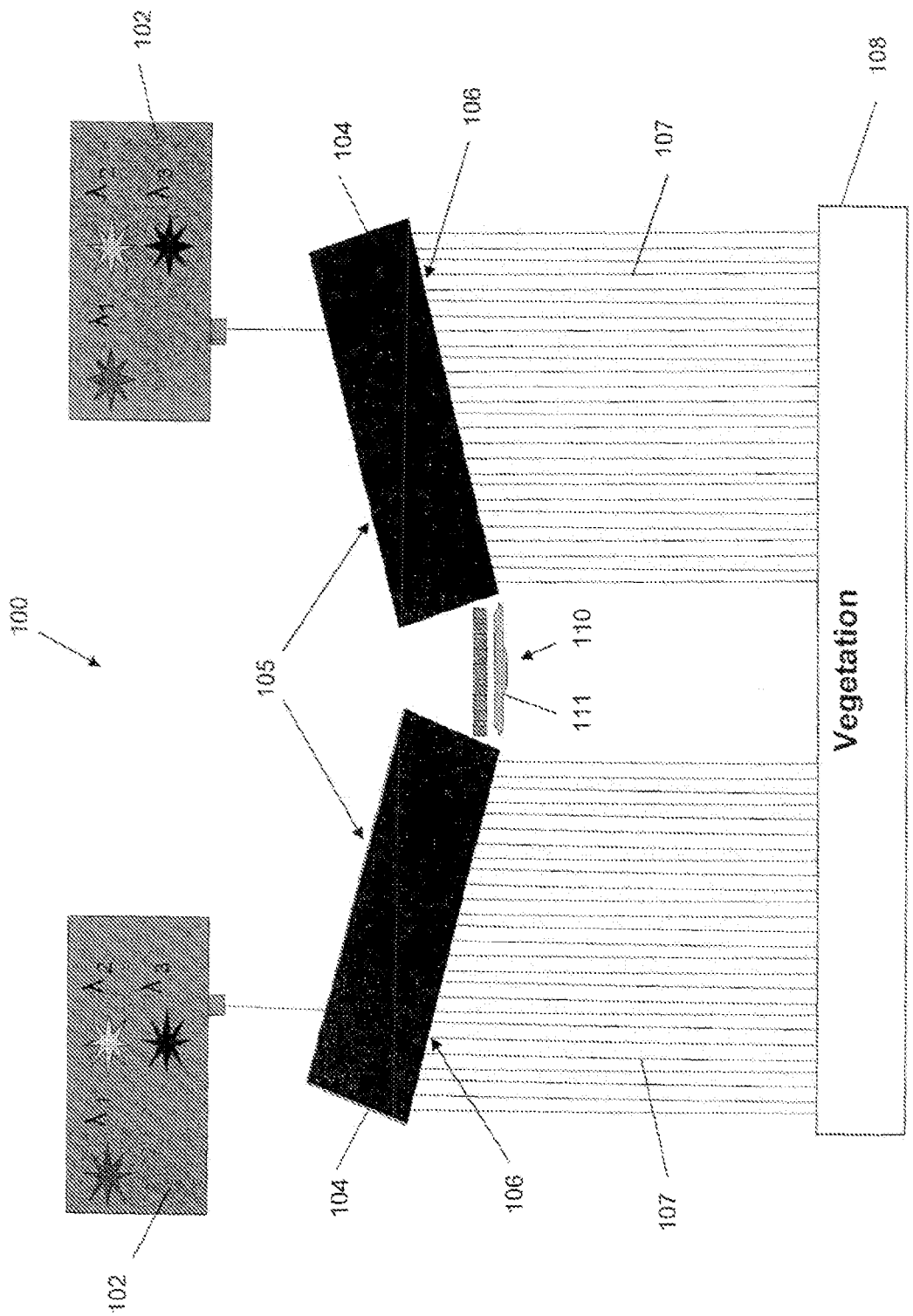
FIGS. 1 and 2 illustrate an optical device in accordance with a specific embodiment of the present invention.
Figure 2:
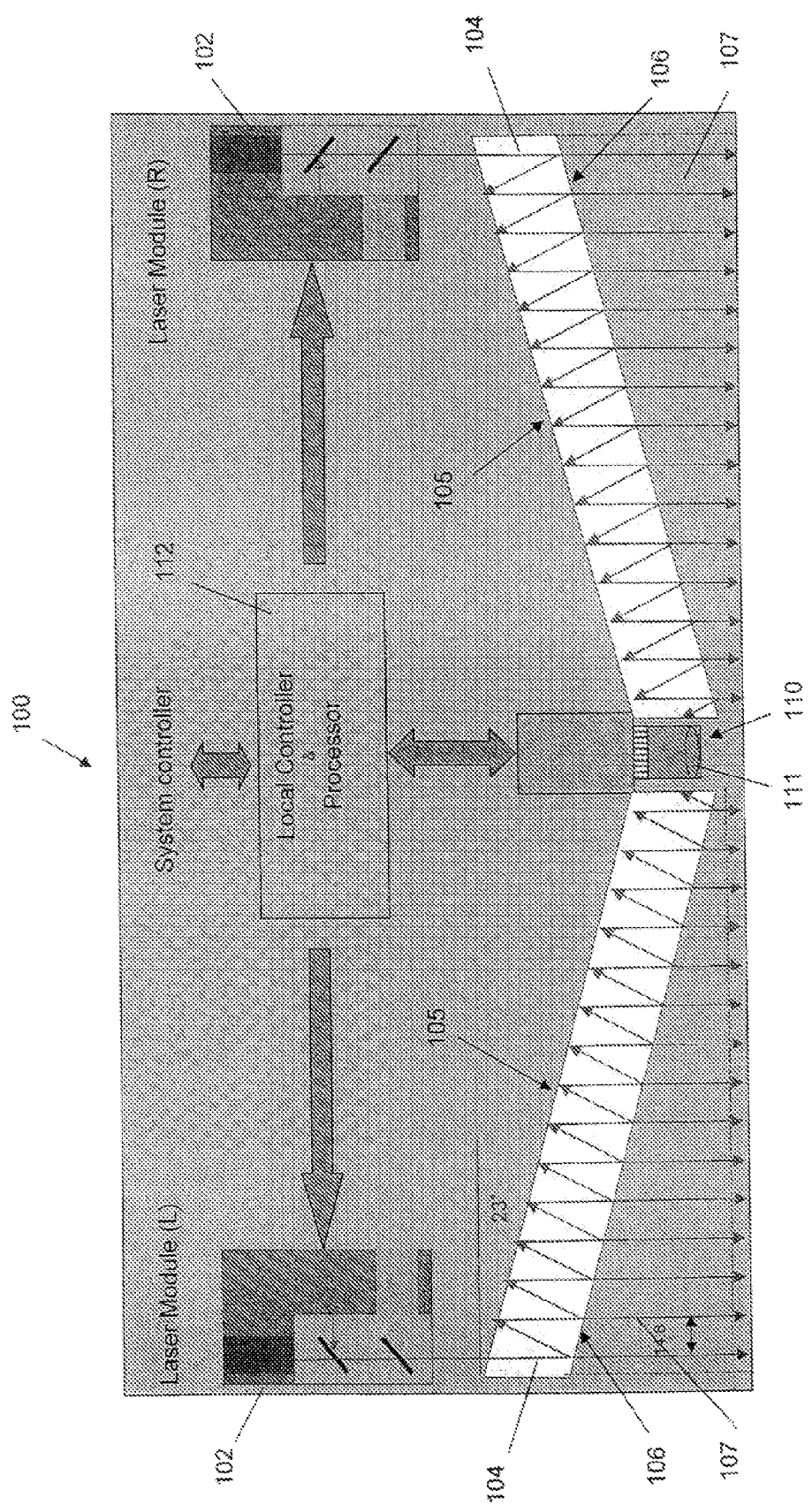

Referring initially to FIGS. 1 and 2 an optical device in accordance with a specific embodiment of the present invention is now described. FIG. 1 shows a schematic top view of an optical device 100 and FIG. 2 shows a schematic cross-sectional view of the device 100 also including additional components. The optical device is in this embodiment arranged to select plant matter, such as weeds, but it will be appreciated that the optical device may alternatively also be arranged to select any other type of matter, such as minerals or another type of organic matter having a specific property.

The optical device comprises a pair of light sources 102, which in this embodiment each comprise laser diodes. The laser diodes provide laser light having respective wavelengths and the light from each light source 102 is combined to one beam that is directed to a respective optical element 104. In this embodiment each light source 102 includes 3 laser diodes generating light having a first wavelength of 635 nm, a second wavelength of 670 nm and a third wavelength of 785 nm. The laser light from the 3 lasers is combined into one combined beam of light for each light source 102. A person skilled in the art will appreciate that alternatively another suitable light source may be used and which may generate light having other suitable wavelengths.

The optical elements 104 are in this example provided in the form of a glass prisms each have opposite reflective coatings 105 and 106. The combined light is reflected between the reflective coatings 105 and 106 in a zigzag manner and the reflective coatings 105 have a relatively high reflectivity, such as 99% or higher. The reflective coatings 106 have lower reflectivities than the reflective coatings 105. The reflective coatings 106 are arranged so that a portion of light is transmitted through the reflective coatings 106 and a series of component light beams 107 is directed towards vegetation 108.

A portion of the component light beams is reflected by the vegetation 108 and detected by an imaging detector 110. The imaging detector 110 comprises a photodiode array, an objective lens and a filter 111. The detector 110 generates an electrical signal that is directed to a local controller 112 and a processing system. In this embodiment the device 100 comprises a pair of light sources 102 and each light source 102 has 3 laser diodes emitting light at the 3 wavelengths. Pairs of corresponding lasers (one from each light source) emitting light having the same wavelength are operated together and in sequence with other pairs of corresponding lasers at a predetermined operation period such as 200 ms or any other suitable time. Consequently, it is possible to correlate a detected intensity with a respective wavelength so that wavelength specific intensity information is obtained by the detector 110.

The output signal from the detector is then processed and ratios of detected intensities at the three wavelengths are compared with corresponding intensities ratios of a library of corresponding intensity ratios for plant matter and a type of plant, such as a weed, can be identified by its specific set of detected intensity ratios.

The detector 110 is an imaging photodiode array detector. An objective lens of the detector 110 is arranged to image spots at which the component beams are reflected by the vegetation 108 onto the photodiode array. In this embodiment the objective lens is arranged so that each spot of reflections at a position approximately 60 cm (±20 cm) below the device 100 are imaged onto respective cells of the photodiode array. Consequently, it is possible to detect intensities arising from respective reflections on the plant matter and, due to the known geometry of the device and the parallel nature of the component light beams, it is possible to determine locations of vegetations at which the light was reflected.

The device 100 typically is positioned on a vehicle (not shown) and is moved over the vegetation 108. From the detection of a movement speed of the vehicle and the above described identification of a location of a reflection along the apparatus 100 it is possible to identify locations of plant matter relative to the moving device 100 and, if required, selectively treat an identified plant, such as a weed.

The selection of plant matter is conducted in an automated manner in a processor of the device 100 by processing an output from the detector 110. The device 100 may also comprise a spray unit or the like that is controlled by the processor and is arranged to selectively spray/treat selected plants, such as weeds.

A person skilled in the art will appreciate that the above described device may be used for selecting any type of matter which may or may not be plant matter.

Figure 3:
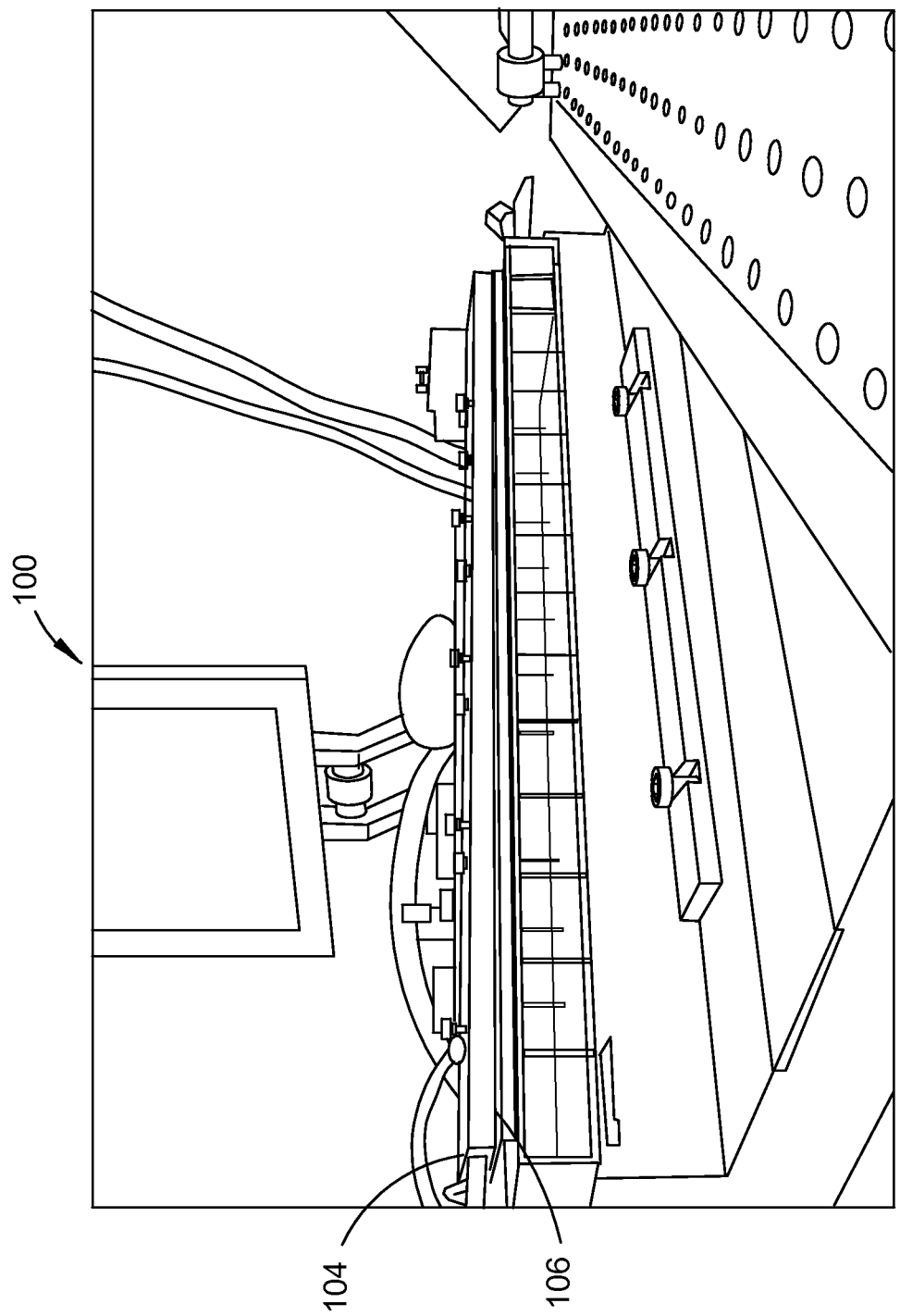
FIG. 3 illustrates a component of the optical device.

Referring again to FIG. 2 and also to FIG. 3, the optical element 104 is now discussed in further detail.

In this embodiment the optical device 104 comprises a glass prism having opposite reflective surfaces 105 and 106. The surfaces 105 has a relatively high reflectivity, such a 99% or higher and the surface 106 comprises a series of surface areas having respective reflectivities and transmissivities. The coatings of the surfaces 105 and 106 comprise layered structures of dielectric materials. At each reflection at the surface 106 a portion of light is transmitted through that surface 106 and consequently light intensity of light that is reflected between the surfaces 105 and 106 in the zigzag manner decreases with an increasing number of reflections. The rectangular prism has a size of approximately 199 mm×29 mm×14 mm and the angle of incidence of the combined beam of light is in this embodiment chosen so that a distance between transmitted component light beam is approximately 15 mm. It will be appreciated that alternatively the prism may have any other suitable dimensions and any other suitable angle of incidence.

If the surface areas of the surface 106 would have identical transmissivities, light intensities of the component beams that are transmitted through the surface portion 106 would decrease with increasing reflections at the surface portion 106. To compensate for that effect the surface areas of the surface 106 have respective transmissivities that increase in the corresponding direction. Each surface area of the surface 106 has a respective coating that has a specific layered structure. Each layered structures may be formed, for example, by $TiO_2$ and/or $SiO_2$ and each layer of a layered structure has a thickness that corresponds to a quarter of a specific wavelength. The layer thicknesses, materials and number of layers of each layered structure are selected so that each surface area has a respective reflectivity and transmissivity for a wavelength range that includes the 3 wavelengths of the light that is emitted by the light sources 102. In the embodiment illustrated in FIG. 3 the surface 106 comprises surface areas having transmissivities that increase from approximately 5% to approximately 40%.

In an alternative embodiment the surface 106 may not comprise discrete surface areas, but may comprise a substantially uniform coating that has a transmissivity that changes in a suitable manner along a length of the surface 106.

It will be appreciated that in alternative variations the optical element 104 may take various different forms. For example, the optical element 104 may not necessarily comprise a glass prism but may be formed from two parallel mirror surfaces having desired reflectivity and transmissivity properties. Further, the optical element may be arranged for generation of any number of component beams and may have any number of surface areas having respective optical properties.

The detector 110 comprises a filter 111 that is arranged for filtering light that is reflected by the plant matter and directed towards the detector 110. In this embodiment the filter 111 has wavelengths windows of increased transmissivity and which are selected so that predominately light having a relatively narrow wavelength ranges that include the wavelengths of light emitted by the laser diodes is transmitted and light having a wavelength outside these wavelength ranges is at least partially absorbed or reflected by the filter 111.

Figure 4:
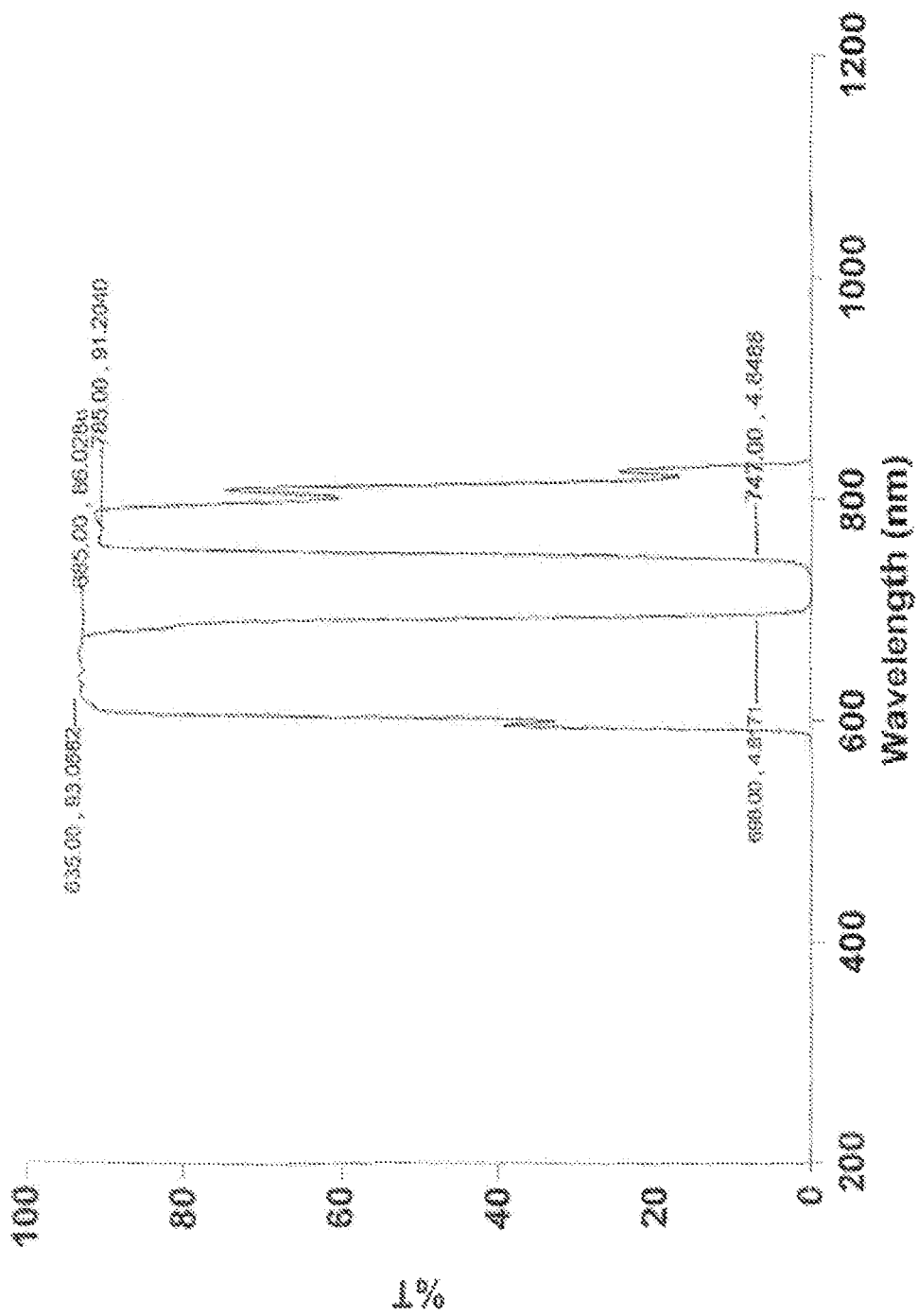
FIG. 4 shows a transmissivity spectrum of a component of the optical device.

The filter 111 comprises thin layered structures of dielectric materials. FIG. 4 shows a transmissivity spectrum of the filter 111. The filter 111 reduces background light intensity fluctuations to which the vegetation 108 is exposed and which consequently form a background for the reflected light. The filter 111 has in this example two transmission windows, but a skilled person will appreciate that the filter 111 may alternatively have only one or more than 2 transmission windows that include the wavelengths at which the lasers emit the light.

The reference that is being made to PCT international application PCT/AU2007/001075 does not constitute an admission that PCT international application PCT/AU2007/001075 is part of the common general knowledge of a skilled person in Australia or any other country.

Although the invention has been described with reference to particular examples, it will be appreciated by those skilled in the art that the invention may be embodied in many other forms.

The invention claimed is:

1. An optical device for selecting specific matter, the device comprising:
 a light source for emitting light having at least 3 wavelengths and for generating a combined beam of light having the at least 3 wavelengths;
 an optical element for receiving the combined beam of light and directing a plurality of component light beams towards matter including the specific matter, the optical element having first surface portions through which the component light beams are respectively directed to matter including the specific matter, the first surface portions having respective optical properties selected so that light transmissivity of the surface portions progressively increases and light intensity differences between the component light beams are thereby reduced; and a detector for detecting reflected component light beams.

2. An optical device as claimed in claim 1, the device comprising:

an optical filter for filtering component light beams that were reflected by the matter including the specific matter, the filter being arranged such that an intensity of the reflected light is reduced in a wavelengths range outside one or more wavelengths ranges that include the at least three wavelengths.

3. The optical device of claim 2 wherein the specific matter is plant matter.

4. The optical device of claim 2 wherein the specific matter is plant matter.

5. The optical device of claim 1 wherein each component light beam is directed through a respective first surface portion.

6. The optical device of claim 1 wherein the optical element is arranged to distribute light intensity from the light source into a plurality of component light beams having substantially same intensity.

7. The optical element of claim 1 wherein the component light beams are substantially parallel.

8. The optical device of any one of claim 1 wherein the optical element comprises second surface portions that are substantially parallel to the respective first surface portions.

9. The optical device of claim 8 wherein the first and second surface portions have reflective coatings and are arranged such that a combined beam of light having the at least three wavelengths is reflected between respective first and second surface portions in a zigzag manner and wherein the optical properties of the first surface portions are transmissivities that are selected such that a component beam of light penetrate through each first surface portion thereby forming a series of component beams of light.

10. The optical device of claim 1 wherein the optical element comprises adjacent first surface portions that have respective optical properties.

11. The optical device of claim 10 wherein the first surface portions of the optical element form a sequence of the first surface portions and each first surface has a surface coating that has a respective transmissivity.

12. The optical device claim 1 wherein the first surface portions of the optical element have a transmissivity that changes along at least a portion of the length of the optical element in a substantially continuous manner.

13. The optical device of claim 1 wherein the optical element comprises a rectangular glass prism.

14. The optical device of claim 1 wherein the first surface portions of the optical device are arranged such that a series of component light beams transmits through the first surface portions and the component light beams have substantially the same intensities and wherein the first surface portions have transmissivities that increase in one direction along at least a portion of the optical element.

15. The optical device of claim 1 comprising a layered structure of a dielectric material having properties selected so that desired transmissivity properties are achieved at a wavelength range that includes the at least three wavelengths of light that is emitted by the light source.

16. The optical device of claim 1 wherein the optical filter is a band pass filter that is arranged to allow transmission of light having a predetermined wavelength range that includes the at least three wavelengths of light emitted by the light source.

* * * * *